United States Patent [19]

Ruell

[11] 4,340,300

[45] Jul. 20, 1982

[54] INPUT SENSOR UNIT FOR A FINGERPRINT IDENTIFICATION SYSTEM

[75] Inventor: Hartwig Ruell, Mount Laurel, N.J.

[73] Assignee: Siemens Corporation, Iselin, N.J.

[21] Appl. No.: 176,696

[22] Filed: Aug. 11, 1980

[51] Int. Cl.$^3$ .......................... G06K 9/00; G06K 9/20
[52] U.S. Cl. ................................................. 356/71
[58] Field of Search .......... 356/71, 371, 394, 239–240; 340/146.3 E; 250/566, 572

[56] References Cited

U.S. PATENT DOCUMENTS

| | | | |
|---|---|---|---|
| 3,138,059 | 6/1964 | White | 356/389 |
| 3,174,414 | 3/1965 | Myer | 356/71 |
| 3,433,940 | 3/1969 | Baez et al. | 362/339 |
| 3,619,060 | 11/1971 | Johnson | 356/71 |
| 3,716,301 | 2/1973 | Caulfield et al. | 356/71 |
| 3,815,998 | 6/1974 | Tietze | 356/371 |
| 3,865,488 | 2/1975 | Del Rio | 356/71 |
| 3,982,836 | 12/1974 | Green et al. | |
| 4,053,228 | 12/1975 | Schiller et al. | |
| 4,120,585 | 11/1976 | DePalma | |

FOREIGN PATENT DOCUMENTS

| | | | |
|---|---|---|---|
| 2846190 | 3/1979 | Fed. Rep. of Germany | 356/71 |
| 898828 | 6/1962 | United Kingdom | 356/239 |

OTHER PUBLICATIONS

Cooper, L., "Coupler for Optical Data", IBM Tech. Disc. Bulletin, vol. 16 #5 10–1973, pp. 1470–1471.

Claassen et al., "Fingertip Orienting & Ridge Viewing Apparatus", IBM Tech. Disc. Bulletin, vol. 8, #3, 8/1965, pp. 435–436.

"Optics" by Hecht & Zajac, edited by Addison-Wesley Publishing Co., p. 481.

Siemens Forschungs-und Entwicklungs-Berichte, vol. 8, No. 5, Springer Verlag 1979, pp. 268–271, R. Koch and H. Herbst.

*Primary Examiner*—William H. Punter
*Attorney, Agent, or Firm*—Spellman, Joel & Pelton

[57] ABSTRACT

There is disclosed an input sensor unit for a fingerprint verification system. A sensor plate facing a fingerbed is composed of a transparent polymer which is elastic so as to form a latent topographic relief of a finger pattern. A sensing light beam is coupled into the sensor plate through one edge surface. An output light beam emitted through a planar surface of the sensor plate at the opposite side of the fingerbed is directed onto the light sensitive area of an electro-optical sensing array. In the optical path of the output light beam there is arranged an optical lens for focusing the output light beam onto the light sensitive area and an optical filter for masking out the direct light of the output light beam.

3 Claims, 9 Drawing Figures

INPUT SENSOR UNIT FOR A FINGERPRINT IDENTIFICATION SYSTEM

BACKGROUND OF THE INVENTION

This invention relates generally to techniques of identifying an individual through the identification of the individual's fingerprints, and more particularly to an input sensor unit of fingerprint verification terminal for obtaining an individual's fingerprint using a dry-process or inkless method.

Fingerprint identification systems which actually do not identify the print of a finger but the finger itself when pressed on a contact surface are well known in the art. U.S. Pat. No. 4,053,228 to Michael Schiller discloses a finger identification apparatus of this type which has a transparent glass plate as contact surface for the finger. A source of spatially coherent light provides an interrogating light beam which is directed through the front surface of the glass plate. The light beam is partially reflected at the back surface of the glass plate when a finger is applied to that surface by virtue of optical discontinuities between the glass plate and the finger. There are two different types of discontinuities: one discontinuity takes place between the glass plate and the air underlying the valleys of the finger. Another discontinuity appears between the glass plate and the finger at the crests of the finger. These discontinuities cause differing amounts of light to be reflected; and a reflected signal beam carrying fingerprint information is thus created. This modulated reflected signal beam is correlated against a hologram of the same fingerprint to provide identification.

It has to be understood that the information content of the reflected light beam is highly dependent on the differences of these discontinuities. The reflected light beam may show poor contrasts between crests and valleys of the fingerprint if the finger is not held absolutely immobile while it is in contact with the glass surface. Further blurring or distortions of the fingerprint may result from differing pressure forces during the process of comparison.

Another fingerprint identification system is disclosed in U.S. Pat. No. 4,120,585 to De Palma et al. This invention relates to a pliable optical prism in a fingerprint sensing terminal, the face of which prism is contacted by a finger. Basically the invention comprises an optical element which is to some extend deformable in response to finger pressure, thereby increasing its contact area with a finger. The optical element regains its original shape when the pressure is removed. By proper contact pressure of the finger, a sensing light beam is partially reflected to a photo sensitive device which is activated thereby. This photosensitive device, in turn, activates the sensing terminal. The only reason for the prism to be pliable is to obtain a positive requirement of sufficient finger pressure for activating the system. This known pliable optical prism though having a rippled surface in operation which acts as mirror, still has a very small topographic relief.

The U.S. Pat. No. 3,982,836 issued to Green et al, discloses a method and means for enhancing prints for direct comparison, which method utilizes a transparent pressure-sensitive gel to capture a print pattern. While pressing the finger on the clear plane surface of the transparent pressure-sensitive gel, in the form of a film or tape, contact with the ridges and grooves of the finger causes a relative severe disturbance of the optical quality of the surface. The system includes an elongated pressure-sensitive tape and means for advancing it to expose successive clear portions, so that a number of print images may be made and retained in a single row. An object print formed in the surface of the tape thus constitutes a long-lasting record. A suitable choice of pressure-sensitive material is suggested to obtain a record which may be considered substantially permanent.

A polarized beam of collimated light is passed through the gel. The pattern features impressed in the surface of the gel scatter light out of the optical path. The beam is then directed to a second polarizing element oriented so as to filter out the scattered light rays and thereby to produce a high-contrast print image for direct viewing or further automated processing.

The various fingerprint sensing systems and techniques do not fulfill all practical requirements of a really simple and feasable sensing device of fingerprint verification system which have to be met to provide an apparatus interrogating fingerprints with the highest quality and best contrast for obtaining undistorted information for storing or comparison purposes.

It is therefore an object of the present invention to provide an improved fingerprint verification terminal.

Another object of the invention is to provide an input sensor unit of a fingerprint verification terminal with optical means capable of high resolution of a fingerprint and an improved discrimination of details of the fingerprint independant of differences in individuals reactions to instructions for use or actual appearances of fingers whose prints are to be verified.

A further object of the invention is to provide a finger print verification terminal which sensing results are independent from lasting residues of fingerprints which may for example remain on surfaces of glass sensing plates or glass sensing prisms and may distort further sensing attempts if they are not removed.

Still another object of the present invention is to provide an inkless dry-process fingerprint verification technique which is easily to be used in high performance protection and safeguard systems.

SUMMARY OF THE INVENTION

In the present invention there is provided an input sensor unit for fingerprint verification systems which has a fingerbed with an opening for receiving a finger, which print is to be verified. A sensor plate having a first and a second large planar surface, and edge surfaces is arranged adjacent and in parallel to the fingerbed covering the opening. The sensor plate is composed of a transparent polymer which is elastic so as to form a latent topographic relief of a finger pattern while exposed to the finger.

Illuminating means are provided for sending a sensing light beam through an edge surface into the sensor plate which light beam is internally totally reflected at the plane parallel surfaces as long as the first planar surface is not exposed to a finger. Local distortions of the first planar surface in the presence of the finger result in reflected light rays which meet the second planar surface at the opposite side of the fingerbed with an angle of incidence smaller than the limiting angle of total reflection. This results in an output light beam modulated by information containing the fingerprint structure.

An electro-optical sensing array, having a light sensitive area, is exposed to this output light beam for converting the modulated output light beam into electrical signals containing the information of the fingerprint. For improving the quality of the image directed onto the light sensitive area of the electro-optical sensing array, optical lens means facing the sensor plate and optical filter means arranged between the lens means and the electro-optical sensing array are adjusted such that a part of the output light beam to be designated as direct light and emitted in a direction perpendicular to the second planar surface of the sensor plate is masked out of the output light beam.

This arrangement has several advantages. Known input sensor units often make use of a clear sensor plate or sensor prism made of glass and a finger pattern formed of skin oil deposits is evaluated. These deposits depend on a variety of factors, as temperature, emotional appearance and age of a person to be tested. Furthermore, the requirement of holding the finger immobile while pressing the sensor surface to obtain high quality prints is another objective which restricts the practical use of known input sensors. The present invention overcomes these restrictions since the planar surface of the sensor plate exposed to a finger forms a latent true topographic relief of the finger pattern which is not disturbed or distorted by oil skin deposits. This latent relief is scanned optically which can be achieved without a complicated optical system utilizing characteristics of internal total reflection in the plane parallel sensor plate.

The source of light producing the sensing light beam can be either coherent or incoherent. According to preferred embodiments of the invention, tubular sources of light, such as fluorescent tubes may be used for producing the sensing light beam. Sources of light can be arranged to face either one or all edge surfaces of the sensor plate, in the latter case, best results of diffused distribution of reflected light are obtained in a relatively small sensor plate. Different mechanical arrangements can be obtained by using cylindrical lenses or total reflection prisms for coupling the sensing light beam into the sensor plate.

The sensor plate itself can be composed of a mixture of elastic polymers such that its index of refraction varies in dependence upon the depth of penetration in the direction perpendicular to its large planar surfaces. The variation of this index of refraction also can be restricted to the depth of penetration of a finger or could be unlimited across the whole depth of the sensor plate.

The quality of the output image, furthermore, can be improved by focusing and spatial filtering techniques in using conventional optical means, such as a knife edge or an optical band-pass filter. Optical lens means focus the modulated output light beam onto the light sensitive area of the electro-optical sensing array which might be either one-dimensional or two-dimensional. Two-dimensional electro-optical sensing arrays also are commercially available and may be preferred, since by a two-dimensional device a relative movement between output light beam and electro-optical sensing array can be avoided.

The described invention, furthermore, has the advantage of being assembled from inexpensive, sturdy elements in a compact arrangement. No movable parts are necessary for sensing a fingerprint and for converting a resulting image into a series of electrical signals containing the image information which can be processed or evaluated in a conventional image processing unit.

BRIEF DESCRIPTION OF THE DRAWINGS

A better understanding of the invention may be had by reference to the following description of preferred embodiments in conjunction with the accompanying drawings, in which.

DESCRIPTION OF PREFERRED EMBODIMENTS

Preferred embodiments of the invention will now be described in detail with reference to FIGS. 1 to 7.

Figure 1:
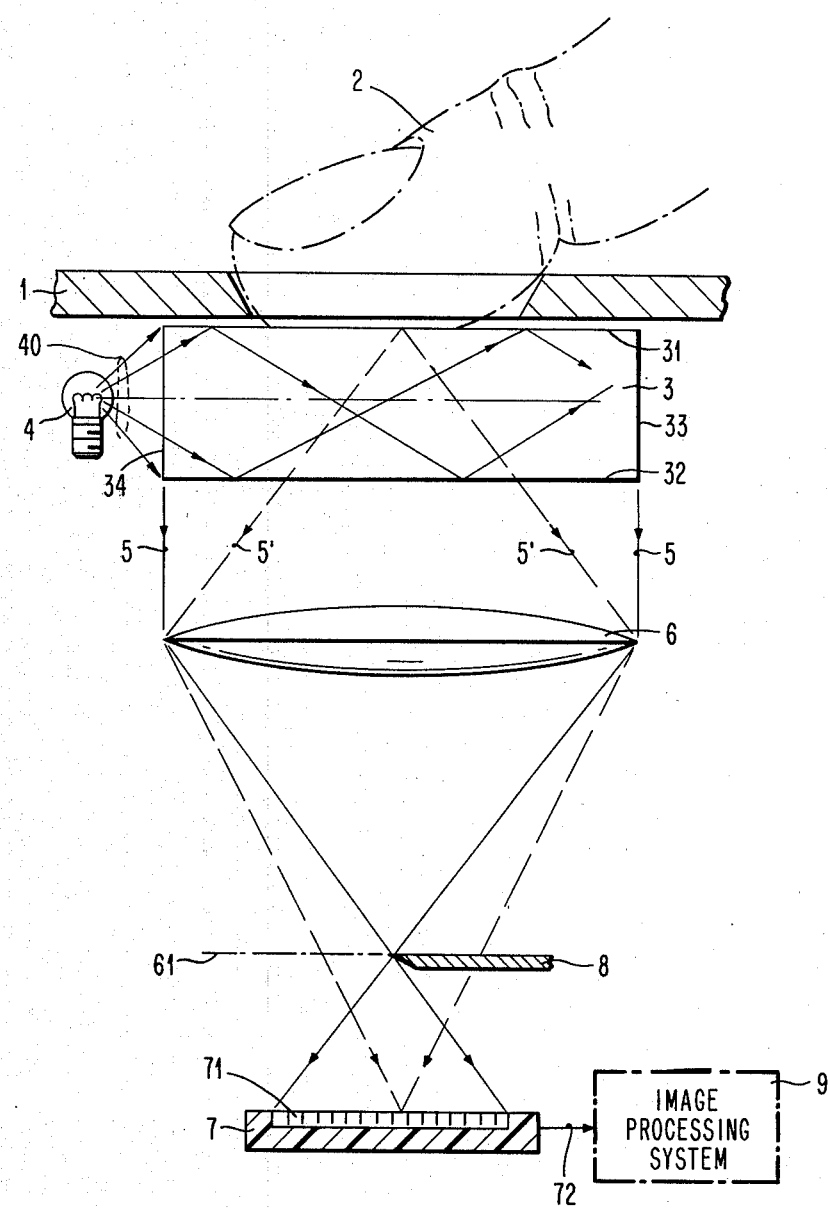
FIG. 1 shows a structural diagram of an input sensor unit according to the present invention having a sensor plate composed of an elastic polymer.

The general structure of an input sensor unit according to the present invention is represented in FIG. 1. It is composed of a fingerbed 1 having a center opening for receiving a finger 2 which is shown in dotted lines 4 for representing an operative condition.

Beneath and in parallel to the fingerbed 1 there is arranged a sensor plate 3. The sensor plate 3 is not shown to scale for the reason of better understanding. It is actually a relatively thin strip of material composed of an elastic polymer having planar surfaces 31 and 32, which are arranged in parallel and perpendicular edge surfaces 33 and 34. The sensor plate 3 is composed of a pressure sensitive elastic polymer. The elastic characteristics of the sensor plate 3 should be as distinct as to obtain a latent true topographic relief of the valleys and crests of a finger while the finger 2 is pressed on the first planar surface 31 directly facing the fingerbed 1. Sensor plates having these characteristics can be obtained from commercially available silicone elastomer, such as silicone elastomer RTV 670 manufactured by General Electric.

Aside of the sensor plate 3 facing one of its edge surfaces 34 there is arranged a source of light 4 generating a sensing light beam which is directed into the sensor plate 3 through the facing edge surface 34. Because of the plane parallel structure of sensor plate 3 light coupled into sensor plate 3 will be distributed within it by internal reflection. As long as the plane parallel structure of the sensor plate 3 is not disturbed, that is in absence of a finger, the sensing light beam will be totally reflected and no light will be emitted by the sensor plate 3. This undistorted condition changes whenever a finger 2 is imposed on the first planar surface 31.

Figure 2:
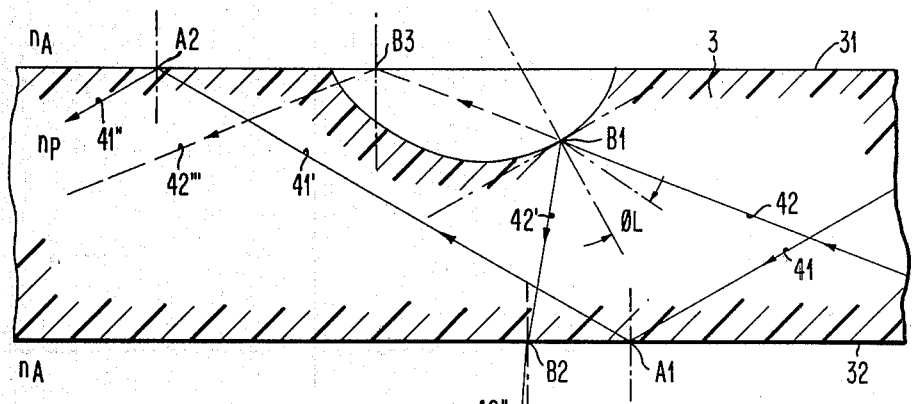
FIG. 2 shows a detail of the sensor plate representing the light distribution within the sensor plate.

The principles of the light distribution of the sensing light beam 40 may be better understood from a more detailed diagram of the sensor plate 3 shown in FIG. 2; for the reason of better perspective just one recess 35 in the first planar surface 31 is shown. This recess 35 may result from a ridge of a finger.

From the optical point of view sensor plate 3 and surrounding air form an optical system composed of three layers. The sensor plate 3, the center layer has an index of refraction $n_P$. Both planar surfaces 31 and 32 face respective air layers having an index of refraction $n_A$. According to Snell's Law in such a system there exists a limiting angle of total reflection which is determined by:

$$\sin\phi_L = n_A/n_P. \quad (1)$$

For the reason of better prespective just two light rays and their reflections and derivatives are shown. A first light ray 41 stands for all rays which are totally internally reflected. This first ray 41 strikes the second planar surface 32 at point A1 with an angle of incidence larger than the limiting angle of reflection $\phi_L$ and is totally reflected into a reflected ray 41'. This ray, in turn, strikes the first planar surface 31 at point A2 and is there again reflected into ray 41'. Since all rays of this group are internally reflected similarly within the sensor plate 3, no light will be emitted into the surrounding areas, i.e. the planar surfaces 31 and 32, respectively viewed in a perpendicular direction will be totally dark.

This condition changes whenever a planar surface is distorted as for example by recess 35. Ray 42 representing the group of rays which strike a locally distorted surface is internally reflected into a reflected ray 42' at point B1, since it meets the tangent plane—as schematically shown—under an angle larger than the limiting angle $\phi_L$ of total reflection. The reflected ray 42' striking the second planar surface 32 at point B2 under an angle of incidence smaller than the limiting angle $\phi_L$ of total reflection is refracted into ray 42'. Without a local distortion of the first planar surface 31 the second ray 42 would strike this surface at point B3 and would also be internally reflected into ray 42'''. This shows that any distortion of the horizontal plane of the first planar surface 31 in presence of a finger results in light rays emitted through the second planar surface 32 of sensor plate 3.

It may be understood that corresponding results may be achieved if the index of refraction $n_P$ of sensor plate 3 varies in dependence upon the depth the penetration of light in a direction perpendicular to the planar surfaces 31 and 32.

Figure 8A:
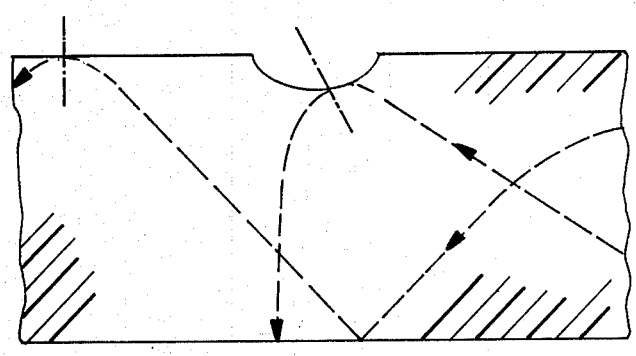
FIGS. 8A and 8B show modified embodiments of the structure of FIG. 2.
Figure 8B:
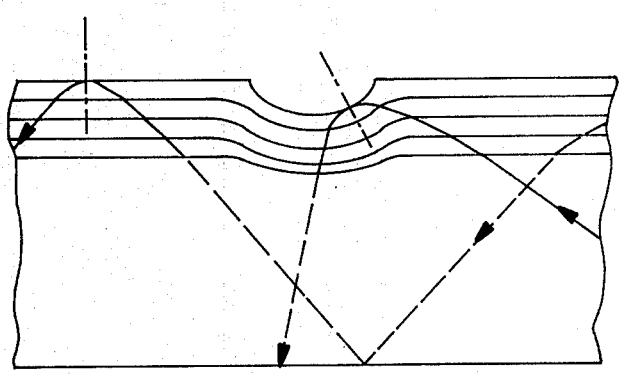

This is illustrated in FIG. 8a. The region of varying index of refraction may be limited to the depth of the deformance of the plate 3, when the finger is pressed on the first surface 31.

Continuing now with the description the arrangement of the input sensor unit as shown in FIG. 1, it is to be seen that sensor plate 3 emits through its second planar surface 32 light which is composed of two light beams: a direct light beam consisting of rays 5 (whose origin will become apparent from the discussion below with respect to FIG. 2) forming a so-called parallel part, and a modulated light beam composed of rays 5' which contain the useful information of the fingerprint.

Both light beams undergo a refraction in an optical lens system 6 facing the second planar surface 32 of the sensor plate 3. For reproducing phase structures resulting from the fingerprint in a photo-sensitive area 71 of an electro-optical sensing array 7 the optical lens system 6 arranged between sensor plate 3 and this electro-optical sensing array 7 is chosen such that the modulated light beam consisting of rays 5' is projected onto the optical sensitive area 71.

Since the direct light beam consisting of rays 5 also contains distortions of phase structures in the focal plane of optical lens system 6, an optical filter is arranged to mask the direct light beam which is focused in this plane. In the embodiment of FIG. 1 the optical filter is formed of a so-called knife edge 8, a conventional means for masking specific parts of a light beam for various objectives. One example is described in "Optics" by Hecht & Zajac, edited by Addison-Wesley Publishing Company, page 481. The knife edge 8 in the arrangement of the present invention is adjusted in the focal plane 61 of the optical lens system 6 such that it obstructs the light beam focused in this plane.

The optical image of phase structures thus represented to the photo-sensitive area 71 of the electro-optical sensing array 7 is converted into electrical signals containing the complete information of the phase structure. For this conversion any conventional electro-optical sensing array may be used. As described in Siemens Forschungs-und Entwicklungs-Berichte, Vol. 8, No. 5, Springer Verlag 1979, pages 268 to 271, such arrays consist of a regular arrangement of photosensitive cells arranged either in a row forming a line of serial sensor array or over an area for parallel applications. For recording an image by line sensor arrays either the array or the object to be recorded must be moved so as to allow line-by-line scanning. This mechanical movement is avoided if a two-dimensional sensor array is used.

Solid-state image sensor arrays of this time are also commercially available, as is the Reticon RA 100×100, a two-dimensional self-scanned optical sensor array having discrete photo-diodes symmetrically arranged into a 100×100 matrix. This array is sold by EG & G Reticon, Sunnyvale, Calif.

Electrical signals 72 representing information of the optical image are transmitted to an image processing system 9 which is schematically shown in dotted lines, thereby indicating that further processing of the electrical signals forms no part of the present invention. According to the explanations in the Background of the Invention, there are known methods and arrangements known to those skilled in the art, for performing the image processing operations. Further description of image signal processing for verifying a fingerprint, therefore, does not seem to be necessary.

In the description of preferred embodiments it was pointed out that optical filter means arranged between the optical lens system 6 and the electro-optical sensor array 7 are very useful for improving the quality of the image represented at the photo-sensitive area 71 of the electro-optical sensor array 7. Since a knife edge, while being very useful for masking the direct light beam, creates some disturbances in the light path, the use of other optical filters may be more preferable.

Figure 3:
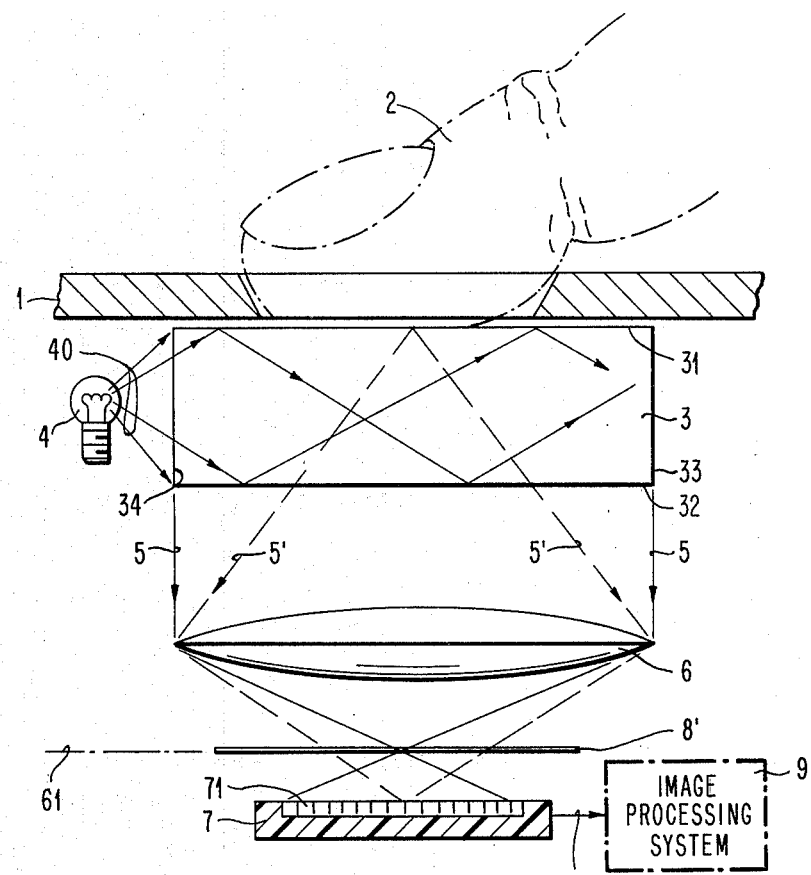
FIG. 3 in combination with FIG. 4 shows another embodiment of the invention with an optical band-pass filter.
Figure 4:
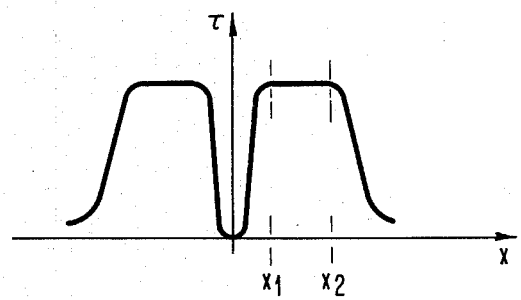

A second embodiment of the invention containing a different type of optical filter is shown in FIG. 3. Comparable elements of both embodiments have identical reference symbols and are identically shown, therefore, the following description is limited to the optical filter used in this second embodiment. It is a conventional optical band-pass filter 8'. It is centered in the focal point of the focal plane 61 of the optical lens system 6. The composition of the optical band-pass filter may be kept from FIG. 4 shown below FIG. 3. FIG. 4 shows a diagram representing the transmission factor $\tau$ versus the distance x from the center point. The transmission characteristic is symmetrical in radial direction. Transmission factor $\tau$ is zero at the center point, increases with growing distance x to this center point up to a maximum which is maintained for a short range between distances x1 and x2, and decreases then sharply with further growing distances from the center point. Such optical band-pass filters are well known to those skilled in the art and the desired transmission characteristic can easily be obtained.

The described characteristic of the optical band-pass filter 8' perfectly meets the present objective. The totally dark center point masks the direct light beam focused in the center point and filters all distortions in a small area surrounding the center point, whereas light directed to the optical band-pass filter in the distance range from $x_1$ to $x_2$ is transmitted without appreciable loss of light. This is the area where the modulated light beam consisting of rays 5' strikes the optical band-pass filter.

Besides the optical filtering of the image presented to the photo-sensitive area of the electro-optical sensing array 7 another essential feature of the present invention is how sensing light beam 40 is generated and coupled into the sensor plate 3. Arrangements for coupling sensing light beam 40 into the sensor plate 3 are schematically represented in FIGS. 5 to 7.

Figure 5:
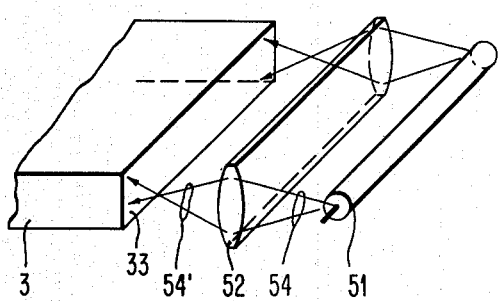
FIG. 5, FIG. 6 and FIG. 7 show further embodiments of the invention for generating a sensing light beam to be directed into the sensor plate.

FIG. 5 shows schematically a three dimensional partial view of sensor plate 3 facing by an edge surface 33 a cylindrical lens 52 arranged with its long axis in parallel to the edge surface. On the opposite side of the cylindrical lens 52 there is provided a tubular source of light 51. Light emitted by this source of light is refracted by the cylindrical lens 52 and directed to the edge surface 33 of the sensor plate 3. The light penetrates into the sensor plate 3 and remains trapped therein, as described above. The reason for the optical coupling arrangement of FIG. 5 is that a reasonably diffused illumination in the direction of the long axis of the edge surface 33 is obtained. As schematically shown by refracted rays 54' which comprise a sensing light beam the distribution of the penetrating light along an axis perpendicular to the long axis of the edge surface also can be kept reasonably diffused.

Figure 6:
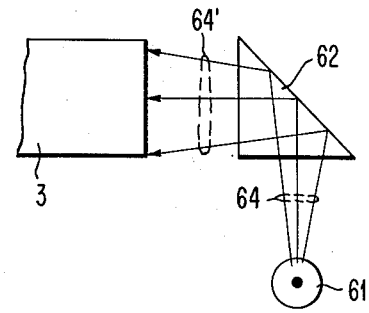
Figure 7:
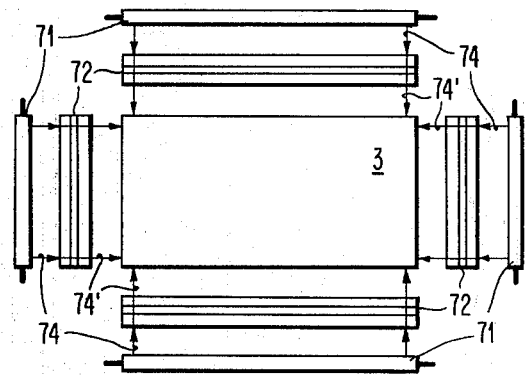

FIG. 6 shows in comparison to the arrangement of FIG. 5 in contrary to a cylindrical lens a total reflection prism 62 arranged between an edge surface 33 of sensor plate 3 and a tubular source of light 61. Since the arrangement of the optical coupling system is such that source of light 61 emits light rays 64 with different angles of incidence smaller than the limiting angle of total reflection the correspondingly reflected rays 64' emerge on different angles from the prism 62 and penetrate the sensor plate 3 through the edge surface 33.

The optical coupling system according to FIG. 6 allows for arranging the source 61 of light aside and beneath or above of the sensor plate 3. In comparison to the arrangement of FIG. 5 thereby a more compact spatial assemblance is achieved.

One of the main characteristic of the optical arrangement for coupling the sensing light beam into the sensor plate 3 is-as has been pointed out-to obtain a diffused distribution of light within the sensor plate. The arrangement represented in FIG. 5 is such that a linear source of light and a cylindrical lens are used to illuminate diffusely a facing edge surface 33. An even better result will be obtained if light is coupled into sensor plate 3 through all four edge surfaces, as it is schematically shown in a top view of the arrangement according to FIG. 7.

This symmetrical arrangement of tubular sources of light 71 and cylindrical lenses 72 guarantees that there is no preferred direction for coupling the sensing light beam into the sensor plate 3. In this case, light is emitted by the tubular sources 71 of light each arranged opposite of an edge surface of sensor plate 3. Four sensing light beams are schematically indicated by rays 74 which are refracted by a respective one of the cylindrical lenses 72 into a refracted light beam 74'. The penetrating light is internally distributed by total reflection and illuminates the pressure sensitive planar surface without any preferred direction, thus resulting in undistorted sensing results.

While the different designs of an input sensor unit and its elements as described constitute preferred embodiments of the invention, it is to be understood that the invention is not limited to these specific design details, and that a variety of changes may be made therein without departing from the scope of the invention.

Many changes, modifications, variations and other uses and applications of the subject invention will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. An input sensor unit for a fingerprint verification system, comprising a sensor plate of transparent pressure-sensitive material having first and second parallel planar surfaces and edge surfaces, the plate deforming when a finger is pressed onto the first surface in such a manner that the parallelism between the first and second surfaces is disturbed in accordance with the contour of the topographic relief of the finger, the sensor plate being composed of a material having an index of refraction which varies in a direction perpendicular to the first and second surfaces in dependence upon the depth of penetration of light; and illuminating means for directing light into the plate through an edge surface, so that the light strikes the undisturbed regions of the first and second surfaces at angles which cause total internal reflection and strikes the disturbed regions of the first and second surfaces at angles which cause light to be transmitted out of the plate through the second surface, whereby the light transmitted through the second surface takes the form of a light beam modulated by the topographic relief of the finger.

2. An input sensor unit as defined in claim 1, wherein the region of varying index of refraction is limited to the depth of the deformance of the plate when a finger is pressed on the first surface.

3. An input sensor unit for a fingerprint verification system, comprising a sensor plate of transparent pressure-sensitive material having first and second parallel planar surfaces and edge surfaces, the plate deforming when a finger is pressed onto the first surface in such a manner that the parallelism between the first and second surfaces is disturbed in accordance with the contour of the topographic relief of the finger, the sensor plate comprising a plurality of layers of material parallel to the first and second surfaces, the respective indices of refraction of the layers increasing in dependence on the distance of the layer from the first planar surface; and illuminating means for directing light into the plate through an edge surface, so that the light strikes the undisturbed regions of the first and second surfaces at angles which cause total internal reflection and strikes the disturbed regions of the first and second surfaces at angles which cause light to be transmitted out of the plate through the second surface, whereby the light transmitted through the second surface takes the form of a light beam modulated by the topographic relief of the finger.

* * * * *